United States Patent [19]
Viola et al.

[11] Patent Number: 5,993,807
[45] Date of Patent: Nov. 30, 1999

[54] TRUNCATED ASPARTASE ENZYME DERIVATIVES AND USES THEREOF

[75] Inventors: Ronald E. Viola, North Canton, Ohio; Maithri M. K. Jayasekera, Ann Arbor, Mich.; Abdullah S. Saribas, Philadelphia, Pa.

[73] Assignee: The University of Akron, Akron, Ohio

[21] Appl. No.: 08/933,222

[22] Filed: Sep. 18, 1997

[51] Int. Cl.$^6$ .............................. A61K 38/51; C12N 9/88
[52] U.S. Cl. .................. 424/94.5; 435/232; 435/252.33; 435/320.1; 536/23.2
[58] Field of Search .......................... 424/94.5; 435/232, 435/252–3, 252.33; 536/23.2, 23.1, 23.7

[56] References Cited

U.S. PATENT DOCUMENTS

| | | | |
|---|---|---|---|
| 4,326,029 | 4/1982 | Yukawa et al. | 435/109 |
| 4,569,911 | 2/1986 | Tsuda | 435/109 |
| 4,692,409 | 9/1987 | Kisumi et al. | 435/109 |

OTHER PUBLICATIONS

Creighton, T. E. Proteins: Structure and Molecular Properties, second edition, W. H. Freeman and Company, New York, p. 422, 1993.

Jayasekera et al. "Enhancement of catalytic activity by gene truncation: Activation of L–aspartase from *Escherichia coli*" Biochem. Biophys. Res. Comm. 238, 411–414, Sep. 18, 1997.

Komatsubara et al., "Overproduction of Aspartase of *Escherichia coli* K–12 by Molecular Cloning," Journal of Biotechnology, v. 3, p. 281–291, (1986).

Mizuta et al., "Alteration of Enzymatic Properties Upon Trypsin–Mediated Activation," Biochimica et Biophysica Acta, v. 452, p. 253–261, (1976).

Shi et al., "The Structure of L–Aspartase Ammonia–Lyase from *Escherichia coli*," Biochemistry, v. 36, p. 9136–9144, (1997).

Jones et al., Recombination and Site–Directed Mutagenesis Using Recombination PCR, Methods in Molecular Biology: PCR Cloning Protocols: From Molecular Cloning to Genetic Engineering (1993), 67:131.

Yumoto et al., Studies on Aspartase, Biochimica et Biophysica Acta (1980) vol. 616:319.

Yumoto et al., Studies on Aspartase VIII. Protease–Mediated Activation: Comparative Survey of Protease Specificity for Activation and Peptide Cleavage, Physiol. Chem. Phys. (1982), 14:391.

Guest et al., Cloning of the Aspartase Gene (aspA) of *Escherichia coli*, Journal of General Microbiology (1984), 130:1271.

Kunkel et al., Rapid and Efficient Site–Specific Mutagenesis without Phenotypic Selection, Methods in Enzymol. (1987), 154:367.

Jones et al., A Precise and Rapid Microtitre Plate Clot Lysis Assay: Methodology, Kinetic Modelling and Measurement of Catalytic Constants for Plasminogen Activation during Fibrinolysis, Thrombosis and Hemostasis (1990), 64:455.

Tarragona–Fiol et al., Identification by Site–Directed Mutagenesis of Amino Acids in the B2 Subsite of Bovine Pancreatic Ribonuclease A, Protein Eng. (1993), 6:901.

Saribas et al., Mutagenic Investigation of Conserved Functional Amino Acids in *Escherichia coli* L–Aspartase, J. of Biol. Chem. (1994), 269:6313.

Sala–Newby et al., Stepwise Removal of the C–Terminal 12 Amino Acids of Firefly Luciferase Resultsin Graded Loss of Activity, Biochem. et Biophys. Acta (1994), 1206–155.

Takagi et al., Cloning and Nucleotide Sequence of the Aspartase Gene of *Escherichia coli*W, Nucleic Acids Res. (1985), 13:2063.

Karsten et al., Purification of Aspartase and Aspartokinase–Homoserine Dehydrogenase I from *Escherichia coli*, Analytical Biochem. (1985), 147:336.

Sjöström et al., Purification and Characterisation of a Plasminogen–Binding Protein from Hemophilus Influenzae. Sequence Determination Reveals Identity with Aspartase, Biochim. et Biophys. Acta (1997), 1324:182.

*Primary Examiner*—Nashaat Nashed
*Attorney, Agent, or Firm*—Renner, Kenner, Greive, Bobak, Taylor & Weber

[57] ABSTRACT

Truncated derivatives of aspartase having enhanced catalytic activity and/or enhanced clot dissolution properties relative to native aspartase from *E. coli*. The enzymes are isolated by site-directed mutagenesis of DNA encoding aspartase. L-aspartic acid is manufactured by contacting fumarate and ammonium ion in the presence of an aspartase derivative.

4 Claims, 1 Drawing Sheet

TRUNCATED ASPARTASE ENZYME DERIVATIVES AND USES THEREOF

This invention was made with government support under a research grant awarded by the National Institutes of Health. The government may have certain rights to the invention.

TECHNICAL FIELD

This invention generally relates to a family of novel derivatives of the aspartase enzyme. More particularly, the present invention relates to truncated derivatives of the aspartase enzyme.

BACKGROUND OF THE INVENTION

Aspartase (L-aspartate ammonia-lyase, E.C. 4.3.1.1) catalyzes the reversible deamination of L-aspartic acid to yield fumarate and ammonium ions (or salts). This dearnination reaction is represented by the Formula I:

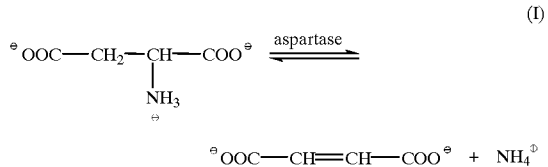

Many plants and microorganisms produce aspartase to control various biological functions such as allowing microorganisms to grow by using glutamate as the only carbon source. The role of aspartase in this process is to recycle aspartic acid for the regeneration of oxaloacetate as an amino group acceptor.

Aspartase is a tetrameric protein with a subunit molecular weight of about 52,400 Da. Its amino acid sequence of aspartase derived from *Escherichia coli* (*E. coli*) has been reported by Takagi et al., *Nucleic Acids Res.* 13:2063 (1985), to be that described in SEQ ID NO: 1. The similar amino acid sequences of aspartase derived from other organisms have also been reported.

The gene that encodes aspartase, aspA, is a polynucleotide sequence of DNA consisting of approximately 1430 base pairs, including a ribosome binding region and a promoter region. The known sequence of this gene for *E. coli* is represented in SEQ ID NO: 1.

Aspartase is an allosteric enzyme having two structural conformations, a high activity form and a low activity forn. At pH values above neutrality, aspartase must be activated by aspartic acid and divalent metal ions in order to catalyze the addition of an ammonium ion across the double bond of fumarate.

Activation by nonspecific proteolytic cleavage of aspartase is also known. Yumoto et al., *Biochim. Biophys. Acta* 616:319 (1980) and Yumoto et al., *Plysiol. Chem. Phys.* 14:391 (1982), for example, have shown that non-specific proteolytic cleavage of peptide bonds near the C-terminal by several different proteases results in a several fold increase of aspartase activity. It was not clear from these studies, however, whether cleavage at a single site or multiple sites was responsible for the enhanced activity and if so, which ones.

It has been observed for the vast majority of enzymes, in contrast to the results observed with aspartase, that the removal of amino acids causes a decrease in the activity of the enzyme. As reported by Sala-Newby et al., *Biochim. Biophys. Acta Protein Struct. MoL Enzymol.* 1206:155 (1994), for example, the sequential removal of amino acids from the C-terminal of firefly luciferase leads to a stepwise loss of bioluminescent activity without regard to the nature or identity of the amino acid that is removed.

Aspartase is used commercially primarily to produce large quantities of L-aspartic acid. L-aspartic acid is used, for example, to produce polyaspartase for use in detergents and for the enhancement of nutrient absorption in agricultural applications. L-aspartic acid is also used for the manufacture of biodegradable chelating agents and in the food industry as a component of the artificial sweetener aspartame (NutraSweet®).

Development of a superior enzyme to produce L-aspartic acid faster, cheaper, or both would be a highly desirable improvement over the current art Currently, L-aspartic acid is commercially manufactured using a native or wild-type aspartase enzyme, such as that from *E. coli*. Heretofore, native aspartase was purified by chromatographic techniques, such as described by Karsten et al., *Anal Biochemn.* 147:336 (1985). Thus, there is a need to isolate and purify aspartase derivatives with enhanced catalytic activity that can produce as much aspartic acid in a given time with a lower quantity of enzyme.

Only recently has it been discovered that aspartase plays a role in blood clot dissolution. Sjöström et al., *Biochim Biophys.* Acta 1324:182 (1997), found that a plasmninogen binding protein, identified as aspartase in this organism, stimulates the activation of plasminogen by tissue plasminogen activator (tPA). tPA is a new drug that has been approved for use in the treatment of heart attacks. This drug accelerates the dissolution of blood clots that lead to heart attacks and strokes. Thus, there is a need to isolate and purify derivatives of aspartase with an enhanced capability to aid in the dissolution of blood clots.

SUMMARY OF INVENTION

It is therefore an object of the present invention to provide an aspartase derivative that demonstrates enhanced catalytic activity in the production of L-aspartic acid.

It is another object to provide a purified form of an aspartase derivative with enhanced catalytic activity.

It is yet another object of the present invention to provide a derivative of aspartase that enhances blood clot dissolution.

It is still another object to provide a method of making an aspartase derivative with enhanced catalytic activity.

It is yet another object to provide a method for expressing and purifying an aspartase derivative.

It is an additional object of the present invention to provide a mutant aspA gene whose gene product is an aspartase derivative with enhanced catalytic activity.

It is still another object to provide a method for making a mutant aspA gene whose gene product is an aspartase derivative with enhanced catalytic activity.

At least one or more of the foregoing objects, together with the advantages thereof over the known art relating to aspartase derivatives, which shall become apparent from the specification which follows, are accomplished by the invention as hereinafter described and claimed.

In general the present invention provides an enzyme having enhanced catalytic activity, for the conversion of fumarate and ammonium ions to L-aspartic acid, relative to native aspartase from *E. coli*. The present invention also provides an enzyme that aids in blood clot dissolution.

The present invention also includes a method for preparing an aspartase derivative comprising the steps of providing a gene coding for a wild-type aspartase; inserting a stop codon at a position immediately following a codon encoding a positively charge amino acid of the wild-type aspartase, wherein the position of the amino acid is selected from the group consisting of 468, 470 and 471, thereby forming a mutant gene; expressing the mutant gene in an expression system, thereby producing the aspartase derivative; and, optionally, purifying the aspartase derivative.

PREFERRED EMBODIMENT FOR CARRYING OUT THE INVENTION

Figure 1:
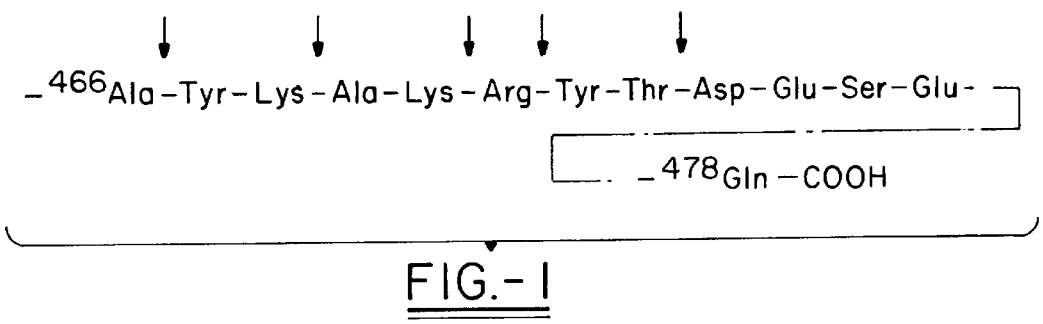
FIG. 1 shows the carboxy-terminal sequence of aspartase with the truncation sites indicated with a (↓)

It has now been found that derivatives of the aspartase enzyme exhibit improved properties over those properties associated with the native or wild-type aspartase enzyme. The expression of these novel enzymes is possible by using recombinant DNA technology. An expression vector, such as pTZ18R, can incorporate the gene that encodes for aspartase using well known restriction enzyme digestion and ligation techniques. Multiple copies of this recombinant expression vector can be introduced into a strain of *E. coli* to generate an overproducing strain that serves as the source for the crude aspartase enzyme.

The novel enzymes of the present invention are similar in structure to the native aspartase enzyme of *E. coli*, the sequence of which is shown in SEQ ID NO: 1, but which have at least one amino acid deleted from the C-terminal end. These derivatives will be referred to as truncated aspartase or aspartase mutants. In the preferred embodiments of the present invention, the truncated enzymes contain at least the first 468 residues of native aspartase.

One preferred embodiment of the present invention is a derivative of aspartase that has been truncated by deleting 7 amino acids from the C-terminal end. Using standard nomenclature, this enzyme will be referred to as Y472stop. The sequence of this truncated enzyme is represented by residues 1–471 of SEQ ID NO: 1.

It has surprisingly been found that the catalytic activity of this enzyme is increased to greater than 100%, preferably to at least about 150%, and even more preferably to at least about 200% of the catalytic activity of native aspartase. By catalytic activity it is meant that the enzyme is capable of catalyzing, in the presence of a substrate and metal ions at pH values above neutrality, the formation of L-aspartic acid from fumarate and ammonium ions.

Typically, the catalytic activity is determined spectrophotometrically and is reported by its rate constant, $k_{cat}$, which is the number of molecules of substrate converted to product per unit time. Preferably, the catalytic activity of the truncated form and the native form are measured in simultaneously run assays under identical conditions in order to avoid assay-to-assay variations in activity by virtue of slight differences in the assay conditions. The effectiveness of a particular mutant enzyme is also reflected in its affinity for substrates as measured by its Michaelis constant, $K_M$, which is the concentration of substrate that gives half maximal reaction velocity. A higher affinity results in a higher effective concentration of the substrate.

Another embodiment of the present invention is directed toward a truncated aspartase enzyme that has 8 amino acids deleted from the C-terminal end of the native enzyme. The sequence of this particular enzyme, which will be referred to hereinafter as R471stop, is represented by residues 1–470 of SEQ ID NO: 1.

As with the Y472stop enzyme, the R471stop enzyme shows increased catalytic activity. Particularly, the catalytic activity of the R471stop enzyme is greater than 100%, preferably at least about 125%, and more preferably at least about 150% of the catalytic activity of native aspartase.

Another embodiment of the present invention is directed toward a truncated aspartase enzyme that has 5 amino acids deleted from the C-terminal end of the native enzyme. The sequence of this particular enzyme, which will be referred to hereinafter as D474stop, is represented by residues 1–473 of SEQ ID NO: 1. The catalytic activity of the D474stop enzyme is greater than 100% of the catalytic activity of native aspartase.

Yet another embodiment of the present invention is directed toward a truncated aspartase derivative that has 10 amino acids deleted from the C-terminal end. This enzyme, which will be referred to hereinafter as A469stop, is represented by residues 1–468 of SEQ ID NO: 1.

Surprisingly, this particular truncated aspartase enzyme has demonstrated the potential for enhanced clot dissolution properties that are not present in the native aspartase enzyme from *E. Coli*. Without intending to be bound by any particular theory, it is believed that the A469stop enzyme demonstrates its clot dissolution properties by promoting the activation of plasminogen to plasmin by tissue plasminogen activator (tPA) by binding to plasminogen or to tPA more effectively than the native aspartase enzyme. The resulting activated plasmin will catalytically degrade the fibrin deposits leading to the dissolution of the blood clot. According to the method of Jones et al., *Thrombosis and Haemostasis* 64:455 (1990), which is incorporated herein by reference, activation of plasminogen by tPA shows a dose dependent response in the presence of increasing concentrations of the A469stop mutant enzyme. Promotion of this activation is not observed with native aspartase from *E. coli*.

Also encompassed by the invention is any analog of the truncated aspartase enzymes disclosed herein. In accordance with this invention, the term analog includes an enzyme having amino acid substitutions, additions or deletions that do not eliminate the enzymatic activity of the truncated enzymes disclosed herein. Preferably, the analogs encompassed herein will retain at least about 100%, preferably at least about 150% and even more preferably at least about 200% of the catalytic activity of the truncated enzyme.

Skilled artisans will readily appreciate that an analog of the truncated enzymes disclosed herein can be readily constructed. The analog can be prepared, for example, by exploiting the degeneracy in the genetic code, or by effecting a point mutation that yields an amino acid substitution and/or addition or deletion of non-essential amino acids.

By way of example, an analog preferably includes those proteins having at least about 50%, preferably at least about 85%, and more preferably at least about 90% amino acid homology. In addition, these enzymes all contain the signature amino acid sequence of aspartase-related enzymes. This sequence is known to be Gly-Ser-Ser-Ile-Met-Pro-Ala-Lys.

Therefore, these enzymes still possess substantially similar enzymatic activity as that of the truncated enzymes disclosed herein.

Additional embodiments of this invention include DNA molecules that encode the proteins described herein. These DNA molecules are represented in SEQ ID NO: 2. Specifically, Y472stop is encoded by nucleotides 575-1987; R471stop is encoded by nucleotides 575-1984; D474stop is encoded by nucleotides 575-1993; A469stop is encoded by nucleotides 575-1978.

Those skilled in the art will appreciate that, based on the redundancy in the genetic code, many different DNA molecules can encode a single protein, and preferred codons can be employed for any given expression system. Furthermore, although derivatives of E. coli aspartase and the corresponding DNA sequences are preferred embodiments of the present invention, skilled artisans will realize that derivatives of aspartase derived from the DNA of other organisms may have amino acid substitutions, additions, deletions, or a combination thereof due to slight differences in the DNA sequences among organisms. All such DNA molecules are contemplated within this invention.

The aspartase derivatives of the present invention are obtained by the expression of a mutated form of the aspA gene that encodes aspartase. Charged or polar amino acids were sequentially eliminated from the carboxy terminal end by introducing stop codons at specific positions in the C-terminal region using site-directed mutagenesis techniques such as those described in White (Ed.), *PCR Protocols: Current Methods and Applications* (1993), which is incorporated herein by reference.

In order to obtain a protein or other gene product from a gene, living cells can be used to express the protein. This is commonly done using a plasmid vector into which the altered gene is inserted. The recombinant plasmid is then taken up by a bacterium, preferably from the TG-1 or JRG-1476 E. coli cell line, and the bacterium is then permitted to reproduce in large quantities as described by Guest et al., *J. Gen. Microbiol.* 130:1271 (1984), which is incorporated herein by reference. These transformed bacteria then express the protein in sufficient amount for purification. All of these steps of getting a gene product from a gene are well known.

The following examples merely illustrate the invention and, as such, are not to be considered as limiting the invention set forth in the claims.

GENERAL EXPERIMENTATION

EXAMPLE 1

Production and Expression of Truncated Aspartase in E. coli

The aspA gene from E. coli that encodes aspartase was inserted into a pTZ18R expression vector by cutting the vector at unique KpnI and HindIII restriction sites using well known digestion and ligation techniques, such as those described by Saribas et al., *J. of Biol. Chem.* 269:6313 (1994), incorporated herein by reference. Subsequent site-directed mutagenesis was carried out by using the recombinant circle PCR (RC-PCR) method described by Tarragona-Fiol et al., *Protein Eng.* 6:901 (1993), incorporated herein by reference. This method requires four primers, Le., single-stranded oligonuclotides that are synthesized to contain a mutation. Primers are incubated in pairs such that a mismatch of two to three base pairs is produced.

Alternatively, site-directed mutagenesis was carried out using the method of Kunkel et al., *Methods Enzymol.* 154:367 (1987). This method involves the replacement of thymine with uracil in the wild type strand of DNA. The subsequent destruction of the uracil-containing strand after heteroduplex formation leads to high yields of mutants.

The primers generate stop codons and alter the restriction enzyme sites at the loci of mutation, positions 467, 469, 471, 472, and 474 of the corresponding protein. The mutation at position 469 destroys a BspWI site; the mutations at 471 and 472 create an AccI site, but the mutation at 472 required the creation of a silent mutation at residue 471 because a restriction enzyme site could not be created at the mutation site; and the mutations at positions 467 and 474 create an AflII site. These alterations in the restriction enzyme sites are necessary to facilitate screening of the colonies to locate and identify the presence of these mutations by restriction enzyme analysis.

Gene amplification of the mutated genes was optimized using a twelve buffer optimization kit (Opti-Prime) that varied the sensitive parameters, including $[Mg^{2+}]$, $[K^+]$ and pH. Polymerase chain reaction (PCR) amplification was carried out using native pfu DNA polymerase for its proof-reading ability, and for producing less contamination than either recombinant pfu or tac polymerases. Thin wall tubes were used for effective heat transfer during the thermocycliryg steps. Standard multicycle gene amplification was carried out using techniques similar to these described in U.S. Pat. Nos. 4,683,195 and 4,683,202, which are incorporated herein by reference.

Double-stranded DNA molecules with discrete, cohesive, single-stranded ends were synthesized and analyzed on an agarose gel to determine the optimum conditions for their formation. The products were then extracted from the gel before being recombined to produce recombinant circles in a buffer containing 10 mM Tris-HCl, pH 8.8, 10 mM NaCl and 1 mM EDTA. Denaturing was then performed at 92° C. for 5 minutes before being reannealed for 3 hours at 57° C.

The DNA was then in condition for transformation. The recombinant circle DNA molecules were incubated with competent cells for 1.5 hours and heat shocked at 42° C. for 1.5 minutes. The cells were then kept on ice for 5 minutes before being plated on YT agar plates containing ampicillin. The presence of mutagenic colonies was screened using restriction enzyme mapping, and the mutated region of the DNA of these colonies was sequenced.

EXAMPLE 2

Characterization and Purification of the Bacterially Expressed Truncated Aspartase The C-terminal of each aspartase derivative is shown in FIG. 1 as a theoretical cleavage of native aspartase. All of the derivatives, except the Y467 mutant, were purified by the procedure described by Karsten et al., *Anal. Biochem.* 147:336 (1985), from an overproducing strain of E. coli developed and described by Saribas et al., *J. Biol. Chem.* 269:6313 (1994), both methods being incorporated herein by reference. Due to the low affinity of the Y467 mutant for red-A agarose column used in the published procedure, a similar, modified procedure described by Saribas in his Ph.D. thesis (University of Akron, 1992), incorporated herein by reference, uses a KCl gradient elution from DEAE-sepharose and a Sephacryl-300 gel filtration step.

Figure 2:
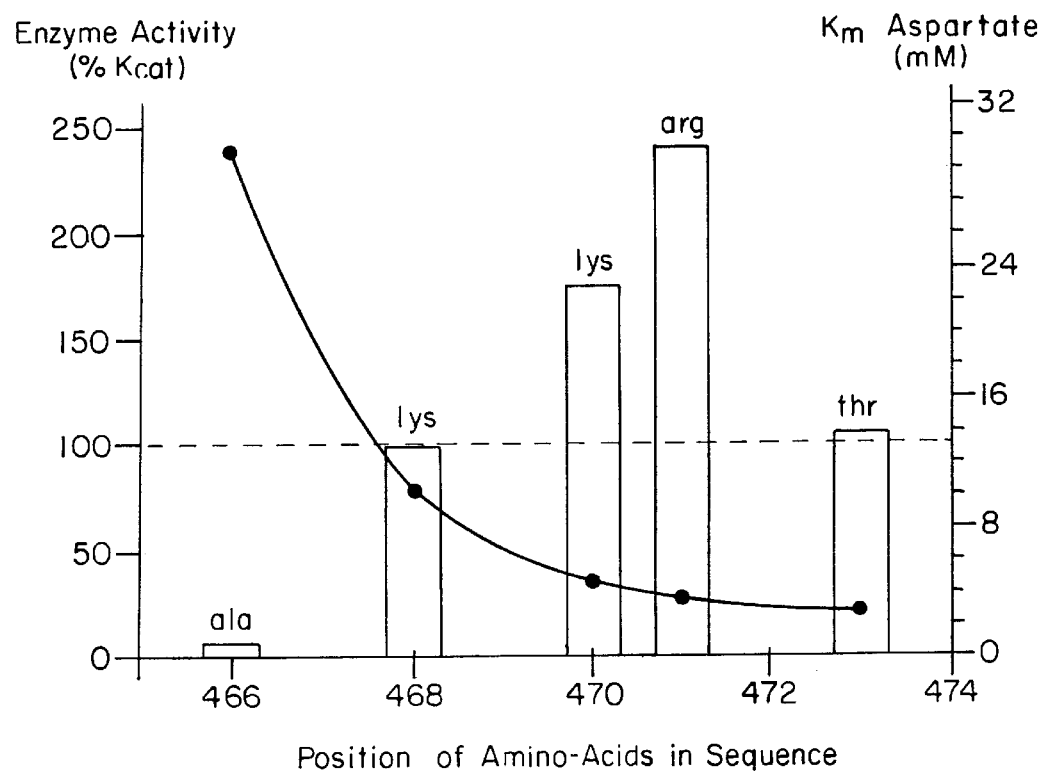
FIG. 2 shows the relationship of the kinetic parameters of aspartase to the identity and position of the carboxy-terminal amino acid. The $K_m$ values of the truncation mutants (•) are shown along with the associated standard errors, and the catalytic activity of the mutants (% $k_{cat}$) are compared in a bar graph to the activity of the native enzyme.

Catalytic activity was determined spectrophotometrically by measuring the formation of fumarate at 240 nm ($E_{240}$= 2.53 mM$^{-1}$ cm$^-$) produced by the enzyme-catalyzed deamination of aspartic acid. A standard assay mix contained 30 mM Hepes buffer, pH 7.0, 10 mM magnesium acetate, and varying concentrations of L-aspartic acid at 30° C. The activity of each mutant was then reported as $k_{cat}$ and the affinity for the substrate as $K_M$ (Table I), as shown in FIG. 2 and Table I.

TABLE I

Kinetic Parameters of Truncated Derivatives of Aspartase

| enzyme mutant | $k_{cat}$ (min$^{-1}$) | percent $k_{cat}$ | $K_M$ (mM) | $k_{cat}/K_M$ | Enhanced Clot Dissolution |
|---|---|---|---|---|---|
| Wild-type | 40.5 ± 1.6 | 100 | 1.8 ± 0.1 | 22.6 ± 0.9 | — |
| D474stop | 42.7 ± 7.6 | 105 | 2.8 ± 1.1 | 15.3 ± 2.9 | — |
| Y472stop | 97.2 ± 6.1 | 240 | 3.3 ± 0.8 | 29.5 ± 1.8 | — |
| R471stop | 70.7 ± 2.9 | 175 | 4.5 ± 0.5 | 15.7 ± 0.6 | — |
| A469stop | 39.6 ± 1.0 | 98 | 10.2 ± 0.7 | 3.9 ± 0.1 | yes |
| Y467stop | 2.5 ± 0.8 | 6.1 | 31 ± 8.2 | 0.08 ± 0.003 | — |

Based upon the foregoing disclosure, it should now be apparent that the use of the enzymes described herein will carry out the objects set forth hereinabove. It is therefore to be understood that any variations evident fall within the scope of the claimed invention. In particular, other means for isolating and purifying the enzymes can be substituted for the techniques described hereinabove. Thus, the scope of the invention shall include all modifications and variations that may fall within the scope of the attached claims.

SEQUENCE LISTINGS

Amino and nucleic acid Sequence of the Sequence Listings are identified as follows:

(a) SEQ ID NO: 1 shows the amino acid sequence of the native aspartase enzyme of *E. coli.*

(b) SEQ ID NO: 2 shows the nucleotide sequence of *E. coli* in the region containing the aspartase gene.

What is claimed is:

1. An enzmye consisting of a truncated *E. coli* aspartase having an amino acid sequence represented by residues 1–468 of SEQ ID NO: 1.

2. The enzyme of claim 1, wherein the enzyme has enhanced clot dissolution capabilities relative to native aspartase from *E. coli*.

3. A method for dissolving a blood clot comprising the step of adding an aspartase derivative to plasminogen and tissue plasminogen activator, thereby enhancing the production of plasmin and enhancing dissolution of the blood clot, wherein said truncated *E. coli* aspartase derivative consists of the amino acid sequence represented by residues 1–468 of SEQ ID NO: 1.

4. A pharmaceutical composition containing the truncated *E. coli* aspartase derivative of claim 1.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 478 amino acids
      (B) TYPE: amino acid
      (C) STRANDEDNESS: single
      (D) TOPOLOGY: linear (ii) MOLECULE TYPE: protein (iii) HYPOTHETICAL: - no (iv) ANTI-SENSE: - no (vi) ORIGINAL SOURCE:
      (A) ORGANISM: Escherichia coli
      (C) INDIVIDUAL ISOLATE: K12
      (G) CELL TYPE: unicellular organism (xi) SEQUENCE DESCRIPTION: SEQ ID NO:1:

```
Met Ser Asn Asn Ile Arg Ile Glu Glu Asp Leu Leu Gly Thr Arg Glu
1               5                   10                  15

Val Pro Ala Asp Ala Tyr Tyr Gly Val His Thr Leu Arg Ala Ile Val
            20                  25                  30

Asn Phe Tyr Ile Ser Asn Asn Lys Ile Ser Asp Ile Pro Glu Phe Val
        35                  40                  45

Arg Gly Met Val Met Val Lys Lys Ala Ala Ala Met Ala Asn Lys Glu
    50                  55                  60

Leu Gln Thr Ile Pro Lys Ser Val Ala Asn Ala Ile Ile Ala Ala Cys
65                  70                  75                  80
```

```
Asp Glu Val Leu Asn Asn Gly Lys Cys Met Asp Gln Phe Pro Val Asp
 85                  90                  95

Val Tyr Gln Gly Gly Ala Gly Thr Ser Val Asn Met Asn Thr Asn Glu
100                 105                 110

Val Leu Ala Asn Ile Gly Leu Glu Leu Met Gly His Gln Lys Gly Glu
115                 120                 125

Tyr Gln Tyr Leu Asn Pro Asn Asp His Val Asn Lys Cys Gln Ser Thr
        130                 135                 140

Asn Asp Ala Tyr Pro Thr Gly Phe Arg Ile Ala Val Tyr Ser Ser Leu
145                 150                 155                 160

Ile Lys Leu Val Asp Ala Ile Asn Gln Leu Arg Glu Gly Phe Glu Arg
165                 170                 175

Lys Ala Val Glu Phe Gln Asp Ile Leu Lys Met Gly Arg Thr Gln Leu
        180                 185                 190

Gln Asp Ala Val Pro Met Thr Leu Gly Gln Glu Phe Arg Ala Phe Ser
195                 200                 205

Ile Leu Leu Lys Glu Glu Val Lys Asn Ile Gln Arg Thr Ala Glu Leu
        210                 215                 220

Leu Leu Glu Val Asn Leu Gly Ala Thr Ala Ile Gly Thr Gly Leu Asn
225                 230                 235                 240

Thr Pro Lys Glu Tyr Ser Pro Leu Ala Val Lys Lys Leu Ala Glu Val
245                 250                 255

Thr Gly Phe Pro Cys Val Pro Ala Glu Asp Leu Ile Glu Ala Thr Ser
        260                 265                 270

Asp Cys Gly Ala Tyr Val Met Val His Gly Ala Leu Lys Arg Leu Ala
275                 280                 285

Val Lys Met Ser Lys Ile Cys Asn Asp Leu Arg Leu Leu Ser Ser Gly
        290                 295                 300

Pro Arg Ala Gly Leu Asn Glu Ile Asn Leu Pro Glu Leu Gln Ala Gly
305                 310                 315                 320

Ser Ser Ile Met Pro Ala Lys Val Asn Pro Val Val Pro Glu Val Val
325                 330                 335

Asn Gln Val Cys Phe Lys Val Ile Gly Asn Asp Thr Thr Val Thr Met
        340                 345                 350

Ala Ala Glu Ala Gly Gln Leu Gln Leu Asn Val Met Glu Pro Val Ile
355                 360                 365

Gly Gln Ala Met Phe Glu Ser Val His Ile Leu Thr Asn Ala Cys Tyr
        370                 375                 380

Asn Leu Leu Glu Lys Cys Ile Asn Gly Ile Thr Ala Asn Lys Glu Val
385                 390                 395                 400

Cys Glu Gly Tyr Val Tyr Asn Ser Ile Gly Ile Val Thr Tyr Leu Asn
405                 410                 415

Pro Phe Ile Gly His His Asn Gly Asp Ile Val Gly Lys Ile Cys Ala
        420                 425                 430

Glu Thr Gly Lys Ser Val Arg Glu Val Val Leu Glu Arg Gly Leu Leu
435                 440                 445

Thr Glu Ala Glu Leu Asp Asp Ile Phe Ser Val Gln Asn Leu Met His
        450                 455                 460

Pro Ala Tyr Lys Ala Lys Arg Tyr Thr Asp Glu Ser Glu Gln
465                 470                 475
```

(2) INFORMATION FOR SEQ ID NO:2:

(i) SEQUENCE CHARACTERISTICS:
        (A) LENGTH: 2280 bp (B) TYPE: nucleic acid
        (C) STRANDEDNESS: single
        (D) TOPOLOGY: linear (ii) MOLECULE TYPE: genomic DNA (iii) HYPOTHETICAL: - no (iv) ANTI-SENSE: - no (vi) ORIGINAL SOURCE:
        (A) ORGANISM: Escherichia coli
        (C) INDIVIDUAL ISOLATE: K12
        (G) CELL TYPE: unicellular organism (xi) SEQUENCE DESCRIPTION: SEQ ID NO:2:

```
TGATCAGCGA AACACTTTTA ATCATCTCCG CCGCTGGGTT TTCACCCGCC GCCATTTTTT     60

GCTGCATCAG CACGAAATTC TTAAAGCCCT GGTTACGTAC CAGTGACATA CCGATAACTG    120

ACGTGAATAT AACCAGCACG AGGGTCAGCA ATACCCCCAA TACATGGGCA ACCTGAATAA    180

AGATTGAAAT CTCAATATAG ACATAAAGGA AAATGGCAAT AAAAGGTAAC CAGCGCAAAG    240

GTTTCTCCTG TAATAGCAGC CGGTTAACCC CGGCTACCTG AATGGGTTGC GAATCGCGTT    300

TAGCTTATAT TGTGGTCATT AGCAAAATTT CAAGATGTTT GCGCAACTAT TTTTGGTAGT    360

AATCCCAAAG CGGTGATCTA TTTCACAAAT TAATAATTAA GGGGTAAAAA CCGACACTTA    420

AAGTGATCCA GATTACGGTA GAAATCCTCA AGCAGCATAT GATCTCGGGT ATTCGGTCGA    480

TGCAGGGGAT AATCGTCGGT CGAAAAACAT TCGAAACCAC ATATATTCTG TGTGTTTAAA    540

GCAAATCATT GGCAGCTTGA AAAGAAGGT TCAC ATG TCA AAC AAC ATT CGT ATC     595
                                     Met Ser Asn Asn Ile Arg Ile
                                      1               5
```

| | |
|---|---|
| GAA GAA GAT CTG TTG GGT ACC AGG GAA GTT CCA GCT GAT GCC TAC TAT<br>Glu Glu Asp Leu Leu Gly Thr Arg Glu Val Pro Ala Asp Ala Tyr Tyr<br>10               15               20 | 643 |
| GGT GTT CAC ACT CTG AGA GCG ATT GTA AAC TTC TAT ATC AGC AAC AAC<br>Gly Val His Thr Leu Arg Ala Ile Val Asn Phe Tyr Ile Ser Asn Asn<br>     25              30               35 | 691 |
| AAA ATC AGT GAT ATT CCT GAA TTT GTT CGC GGT ATG GTA ATG GTT AAA<br>Lys Ile Ser Asp Ile Pro Glu Phe Val Arg Gly Met Val Met Val Lys<br>40               45              50           55 | 739 |
| AAA GCC GCA GCT ATG GCA AAC AAA GAG CTG CAA ACC ATT CCT AAA AGT<br>Lys Ala Ala Ala Met Ala Asn Lys Glu Leu Gln Thr Ile Pro Lys Ser<br>60               65              70 | 787 |
| GTA GCG AAT GCC ATC ATT GCC GCA TGT GAT GAA GTC CTG AAC AAC GGA<br>Val Ala Asn Ala Ile Ile Ala Ala Cys Asp Glu Val Leu Asn Asn Gly<br>     75              80              85 | 835 |
| AAA TGC ATG GAT CAG TTC CCG GTA GAC GTC TAC CAG GGC GGC GCA GGT<br>Lys Cys Met Asp Gln Phe Pro Val Asp Val Tyr Gln Gly Gly Ala Gly<br>90               95             100 | 883 |
| ACT TCC GTA AAC ATG AAC ACC AAC GAA GTG CTG GCC AAT ATC GGT CTG<br>Thr Ser Val Asn Met Asn Thr Asn Glu Val Leu Ala Asn Ile Gly Leu<br>105              110            115 | 931 |
| GAA CTG ATG GGT CAC CAA AAA GGT GAA TAT CAG TAC CTG AAC CCG AAC<br>Glu Leu Met Gly His Gln Lys Gly Glu Tyr Gln Tyr Leu Asn Pro Asn<br>120              125          130            135 | 979 |
| GAC CAT GTT AAC AAA TGT CAG TCC ACT AAC GAC GCC TAC CCG ACC GGT<br>Asp His Val Asn Lys Cys Gln Ser Thr Asn Asp Ala Tyr Pro Thr Gly<br>140              145          150 | 1027 |
| TTC CGT ATC GCA GTT TAC TCT TCC CTG ATT AAG CTG GTA GAT GCG ATT<br>Phe Arg Ile Ala Val Tyr Ser Ser Leu Ile Lys Leu Val Asp Ala Ile<br>155              160            165 | 1075 |
| AAC CAA CTG CGT GAA GGC TTT GAA CGT AAA GCT GTC GAA TTC CAG GAC | 1123 |

```
                                                      -continued

Asn Gln Leu Arg Glu Gly Phe Glu Arg Lys Ala Val Glu Phe Gln Asp
170                 175                 180

ATC CTG AAA ATG GGT CGT ACC CAG CTG CAG GAC GCA GTA CCG ATG ACC    1171
Ile Leu Lys Met Gly Arg Thr Gln Leu Gln Asp Ala Val Pro Met Thr
            185                 190                 195

CTC GGT CAG GAA TTC CGC GCT TTC AGC ATC CTG CTG AAA GAA GAA GTG    1219
Leu Gly Gln Glu Phe Arg Ala Phe Ser Ile Leu Leu Lys Glu Glu Val
200                 205                 210                 215

AAA AAC ATC CAA CGT ACC GCT GAA CTG CTG CTG GAA GTT AAC CTT GGT    1267
Lys Asn Ile Gln Arg Thr Ala Glu Leu Leu Leu Glu Val Asn Leu Gly
220                 225                 230

GCA ACA GCA ATC GGT ACT GGT CTG AAC ACG CCG AAA GAG TAC TCT CCG    1315
Ala Thr Ala Ile Gly Thr Gly Leu Asn Thr Pro Lys Glu Tyr Ser Pro
            235                 240                 245

CTG GCA GTG AAA AAA CTG GCT GAA GTT ACT GGC TTC CCA TGC GTA CCG    1363
Leu Ala Val Lys Lys Leu Ala Glu Val Thr Gly Phe Pro Cys Val Pro
250                 255                 260

GCT GAA GAC CTG ATC GAA GCG ACC TCT GAC TGC GGC GCT TAT GTT ATG    1411
Ala Glu Asp Leu Ile Glu Ala Thr Ser Asp Cys Gly Ala Tyr Val Met
            265                 270                 275

GTT CAC GGC GCG CTG AAA CGC CTG GCT GTG AAG ATG TCC AAA ATC TGT    1459
Val His Gly Ala Leu Lys Arg Leu Ala Val Lys Met Ser Lys Ile Cys
280                 285                 290                 295

AAC GAC CTG CGC TTG CTC TCT TCA GGC CCA CGT GCC GGC CTG AAC GAG    1507
Asn Asp Leu Arg Leu Leu Ser Ser Gly Pro Arg Ala Gly Leu Asn Glu
300                 305                 310

ATC AAC CTG CCG GAA CTG CAG GCG GGC TCT TCC ATC ATG CCA GCT AAA    1555
Ile Asn Leu Pro Glu Leu Gln Ala Gly Ser Ser Ile Met Pro Ala Lys
            315                 320                 325

GTA AAC CCG GTT GTT CCG GAA GTG GTT AAC CAG GTA TGC TTC AAA GTC    1603
Val Asn Pro Val Val Pro Glu Val Val Asn Gln Val Cys Phe Lys Val
330                 335                 340

ATC GGT AAC GAC ACC ACT GTT ACC ATG GCA GCA GAA GCA GGT CAG CTG    1651
Ile Gly Asn Asp Thr Thr Val Thr Met Ala Ala Glu Ala Gly Gln Leu
            345                 350                 355

CAG TTG AAC GTT ATG GAG CCG GTC ATT GGC CAG GCC ATG TTC GAA TCC    1699
Gln Leu Asn Val Met Glu Pro Val Ile Gly Gln Ala Met Phe Glu Ser
360                 365                 370                 375

GTT CAC ATT CTG ACC AAC GCT TGC TAC AAC CTG CTG GAA AAA TGC ATT    1747
Val His Ile Leu Thr Asn Ala Cys Tyr Asn Leu Leu Glu Lys Cys Ile
380                 385                 390

AAC GGC ATC ACT GCT AAC AAA GAA GTG TGC GAA GGT TAC GTT TAC AAC    1795
Asn Gly Ile Thr Ala Asn Lys Glu Val Cys Glu Gly Tyr Val Tyr Asn
            395                 400                 405

TCT ATC GGT ATC GTT ACT TAC CTG AAC CCG TTC ATC GGT CAC CAC AAC    1843
Ser Ile Gly Ile Val Thr Tyr Leu Asn Pro Phe Ile Gly His His Asn
410                 415                 420

GGT GAC ATC GTG GGT AAA ATC TGT GCC GAA ACC GGT AAG AGT GTA CGT    1891
Gly Asp Ile Val Gly Lys Ile Cys Ala Glu Thr Gly Lys Ser Val Arg
            425                 450                 455

GAA GTC GTT CTG GAA CGC GGT CTG TTG ACT GAA GCG GAA CTT GAC GAT    1939
Glu Val Val Leu Glu Arg Gly Leu Leu Thr Glu Ala Glu Leu Asp Asp
440                 445                 450                 455

ATT TTC TCC GTA CAG AAT CTG ATG CAC CCG GCT TAC AAA GCA AAA CGC    1987
Ile Phe Ser Val Gln Asn Leu Met His Pro Ala Tyr Lys Ala Lys Arg
460                 465                 470

TAT ACT GAT GAA AGC GAA CAG TAATCGTACA GGGTAGTACA AATAAAAAAG      2038
Tyr Thr Asp Glu Ser Glu Gln
            475

GCACGTCAGA TGACGTGCCT TTTTTCTTGT GAGCAGTAAC TTAAAAATAA CAATCTAATA  2098
```

-continued

```
TCAACTTGTT AAAAAACAAG GAAGGCTAAT ATGCTAGTTG TAGAACTCAT CATAGTTTTG    2158

CTGGCGATCT TCTTGGGCGC CAGATTGGGG GGAATAGGTA TTGGTTTTGC AGGCGGATTG    2218

GGGGTGCTGG TTCTTGCCGC TATTGGCGTT AAACCCGGTA ACATCCCGTT CGATGTCATC    2278

TC                                                                  2280
```